(12) United States Patent
Eskaros et al.

(10) Patent No.: US 8,453,904 B2
(45) Date of Patent: Jun. 4, 2013

(54) APPARATUS FOR SUPPLYING SURGICAL STAPLE LINE REINFORCEMENT

(75) Inventors: Sherif Eskaros, Elkton, MD (US);
Joseph J. DiPietro, Jr., Newark, DE (US); Mary Jo Russell, Wilmington, DE (US); Michael Winterling, Landenberg, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 14 days.

(21) Appl. No.: 12/247,710

(22) Filed: Oct. 8, 2008

(65) Prior Publication Data

US 2009/0095791 A1    Apr. 16, 2009

Related U.S. Application Data

(60) Provisional application No. 60/978,178, filed on Oct. 8, 2007.

(51) Int. Cl.
*A61B 17/03*   (2006.01)

(52) U.S. Cl.
USPC .............. 227/175.1; 227/118.1; 606/148; 606/151

(58) Field of Classification Search
USPC .............. 227/175.1, 181.1; 606/154, 156, 606/215, 291
See application file for complete search history.

(56) References Cited

U.S. PATENT DOCUMENTS

| | | | |
|---|---|---|---|
| D235,174 S * | 5/1975 | Gardner ........................... D3/18 |
| 4,354,628 A | 10/1982 | Green | |
| 5,014,899 A | 5/1991 | Presty et al. | |
| 5,040,715 A | 8/1991 | Green et al. | |
| 5,093,760 A * | 3/1992 | Bedol ........................ 361/679.02 |
| D335,139 S * | 4/1993 | McKay ........................... D19/34 |
| 5,263,629 A * | 11/1993 | Trumbull et al. ........... 227/181.1 |
| 5,397,324 A * | 3/1995 | Carroll et al. ................ 606/139 |
| 5,441,193 A * | 8/1995 | Gravener .................... 227/176.1 |
| 5,503,638 A | 4/1996 | Cooper et al. | |
| 5,542,594 A * | 8/1996 | McKean et al. ............. 227/178.1 |
| 5,549,628 A | 8/1996 | Cooper et al. | |
| 5,575,803 A | 11/1996 | Cooper et al. | |
| 5,702,409 A | 12/1997 | Rayburn et al. | |
| 5,752,965 A | 5/1998 | Francis et al. | |
| 5,766,188 A * | 6/1998 | Igaki .............................. 606/151 |
| 5,769,892 A * | 6/1998 | Kingwell ...................... 606/151 |
| 5,810,855 A | 9/1998 | Rayburn et al. | |
| 5,814,057 A * | 9/1998 | Oi et al. ......................... 606/151 |
| 5,833,695 A * | 11/1998 | Yoon ............................. 606/139 |
| 5,843,096 A * | 12/1998 | Igaki et al. .................... 606/151 |
| 5,902,312 A * | 5/1999 | Frater et al. ................... 606/148 |
| 5,908,427 A | 6/1999 | McKean et al. | |
| 5,964,774 A * | 10/1999 | McKean et al. ............... 606/151 |
| 6,045,560 A * | 4/2000 | McKean et al. ............... 606/139 |

(Continued)

FOREIGN PATENT DOCUMENTS

| DE | 199 24 311 A1 | 11/2000 |
|---|---|---|
| EP | 0 667119 A1 | 8/1995 |

(Continued)

*Primary Examiner* — Hemant M Desai
*Assistant Examiner* — Gloria R Weeks
(74) *Attorney, Agent, or Firm* — Andrea W. Burke (57) ABSTRACT

An apparatus for supplying surgical buttress material to a surgical stapler is provided. The apparatus has a pivotable area for attaching surgical buttress material. The apparatus may also have an adhesive and a release liner disposed over the buttress material.

17 Claims, 11 Drawing Sheets

U.S. PATENT DOCUMENTS

| | | | |
|---|---|---|---|
| 6,063,097 A * | 5/2000 | Oi et al. | 606/151 |
| 6,099,551 A * | 8/2000 | Gabbay | 606/219 |
| 6,120,492 A * | 9/2000 | Finch et al. | 604/502 |
| 6,273,897 B1 * | 8/2001 | Dalessandro et al. | 606/139 |
| 6,325,810 B1 * | 12/2001 | Hamilton et al. | 606/151 |
| 6,503,257 B2 * | 1/2003 | Grant et al. | 606/151 |
| 6,592,597 B2 | 7/2003 | Grant et al. | |
| 6,638,285 B2 * | 10/2003 | Gabbay | 606/151 |
| 6,704,210 B1 | 3/2004 | Myers | |
| 6,730,299 B1 * | 5/2004 | Tayot et al. | 424/45 |
| 6,874,669 B2 * | 4/2005 | Adams et al. | 227/175.1 |
| 6,939,358 B2 | 9/2005 | Palacios et al. | |
| 7,147,138 B2 | 12/2006 | Shelton, IV | |
| 7,377,928 B2 * | 5/2008 | Zubik et al. | 606/151 |
| 7,431,730 B2 | 10/2008 | Viola | |
| 7,559,937 B2 * | 7/2009 | de la Torre et al. | 606/142 |
| 7,665,646 B2 * | 2/2010 | Prommersberger | 227/175.1 |
| 7,721,930 B2 | 5/2010 | McKenna et al. | |
| 7,789,889 B2 | 9/2010 | Zubik et al. | |
| 7,988,027 B2 | 8/2011 | Olson et al. | |
| 8,028,883 B2 | 10/2011 | Stopek | |
| 8,062,330 B2 | 11/2011 | Prommersberger et al. | |
| 2003/0120284 A1 | 6/2003 | Palacios et al. | |
| 2004/0093029 A1 | 5/2004 | Zubik et al. | |
| 2006/0004407 A1 | 1/2006 | Hiles et al. | |
| 2007/0034669 A1 | 2/2007 | de la Torre et al. | |
| 2007/0246505 A1 | 10/2007 | Pace-Floridia et al. | |
| 2008/0169328 A1 | 7/2008 | Shelton | |
| 2008/0290134 A1 | 11/2008 | Bettuchi et al. | |
| 2009/0076528 A1 | 3/2009 | Sgro | |
| 2009/0277944 A9 | 11/2009 | Dalessandro et al. | |
| 2010/0012704 A1 | 1/2010 | Tarinelli Racenet et al. | |
| 2010/0059570 A1 | 3/2010 | Ostapoff et al. | |
| 2010/0072254 A1 | 3/2010 | Aranyl et al. | |
| 2010/0076429 A1 | 3/2010 | Heinrich | |
| 2010/0076489 A1 | 3/2010 | Stopek et al. | |
| 2010/0087840 A1 | 4/2010 | Ebersole et al. | |
| 2010/0234861 A1 | 9/2010 | Oray et al. | |
| 2010/0252612 A1 | 10/2010 | Viola | |
| 2010/0331880 A1 | 12/2010 | Stopek | |
| 2012/0289979 A1 | 11/2012 | Eskaros et al. | |

FOREIGN PATENT DOCUMENTS

| | | |
|---|---|---|
| EP | 1 520 525 A1 | 4/2005 |
| WO | 98/38923 | 9/1998 |
| WO | 02/09593 | 2/2002 |
| WO | 2006/106269 A1 | 10/2006 |

* cited by examiner

APPARATUS FOR SUPPLYING SURGICAL STAPLE LINE REINFORCEMENT

CROSS REFERENCE TO RELATED APPLICATION

This application claims priority to U.S. Provisional Application No. 60/978,178, filed Oct. 8, 2007.

FIELD OF THE INVENTION

The present invention relates to an apparatus for supply of surgical staple line reinforcement material to a surgical stapler.

BACKGROUND OF THE INVENTION

Surgical stapling devices are employed by surgeons to sequentially or simultaneously apply one or more rows of surgical fasteners such as staples or two-part fasteners to body tissue for the purpose of joining segments of body tissue together. Such stapling devices generally consist of a pair of jaws (one being the cartridge side and one being the anvil side) or arm-like structures between which body tissue to be joined is placed. When the instrument is actuated, or "fired," longitudinally moving firing bars contact staple drive members in one of the jaws, thereby pushing surgical staples through body tissue and into an anvil in the opposite jaw which crimps the staples closed. If tissue is to be removed, a knife blade can be provided to cut between lines of staples. Examples of such instruments are described in U.S. Pat. Nos. 4,354,628, 5,014,899 and 5,040,715, teachings of each of which are incorporated herein by reference.

Surgical stapling devices have found widespread application in surgical operations where body tissue must be joined or removed, such as, bariatric, colorectal, and thoracic procedures. When operating on thin tissue, such as thin emphysematous lung tissue, it is important to effectively seal the tissue which can be particularly prone to air leakage. Preventing or reducing air leakage can significantly decrease post operative recovery time. Inhibiting or preventing tearing at the stapled incision site in musculoaponeurotic areas also significantly decreases recovery time.

Thus, structures for use with surgical stapling devices which enhance sealing at the surgical site and/or reduce tissue tearing are desired.

U.S. Pat. Nos. 5,503,638, 5,575,803, 5,549,628, 5,702, 409, 5,810,855 and 5,908,427 describe surgical staple line reinforcement devices and surgical stapling apparatus with tissue bolstering materials.

U.S. Pat. No. 5,752,965 and U.S. Pat. No. 6,939,358 describe apparatus for applying surgical reinforcement material onto the working surface of a surgical stapler without requiring removal of excess material.

The present invention provides a long felt need for an apparatus that quickly and easily applies a thin and flexible surgical reinforcement material to a stapler.

SUMMARY OF THE INVENTION

The present invention is an improved apparatus for quickly and easily applying a thin and flexible surgical reinforcement material to a surgical stapler. The present apparatus comprises a body having a surgical reinforcement material attached to a portion of said body, the portion of the said body having the reinforcement material thereon being pivotable with respect to the remainder of said body. A touch-up pad may be attached to the apparatus, or otherwise provided as part of a kit. The apparatus further comprises a securement for temporarily fixing a surgical reinforcement material to the apparatus. The body of the apparatus may be configured so that orientation of the apparatus body with respect to a surgical stapler is able to be reversed with respect to the first side and the second side of the apparatus body.

The surgical reinforcement material may further comprise an adhesive on the outermost surface of the surgical reinforcement material with respect to said body. The adhesive may be any suitable adhesive including but not limited to a pressure sensitive adhesive.

DETAILED DESCRIPTION OF THE INVENTION

The present invention provides an apparatus for supplying surgical reinforcement material to a surgical stapler.

As shown in FIGS. 1 through 6, the apparatus 1 of the present invention comprises a body 2 sized to provide a surgical stapler with surgical reinforcement material (FIG. 1), on at least a portion of the open stapler arms of the surgical stapler.

Figure 1:
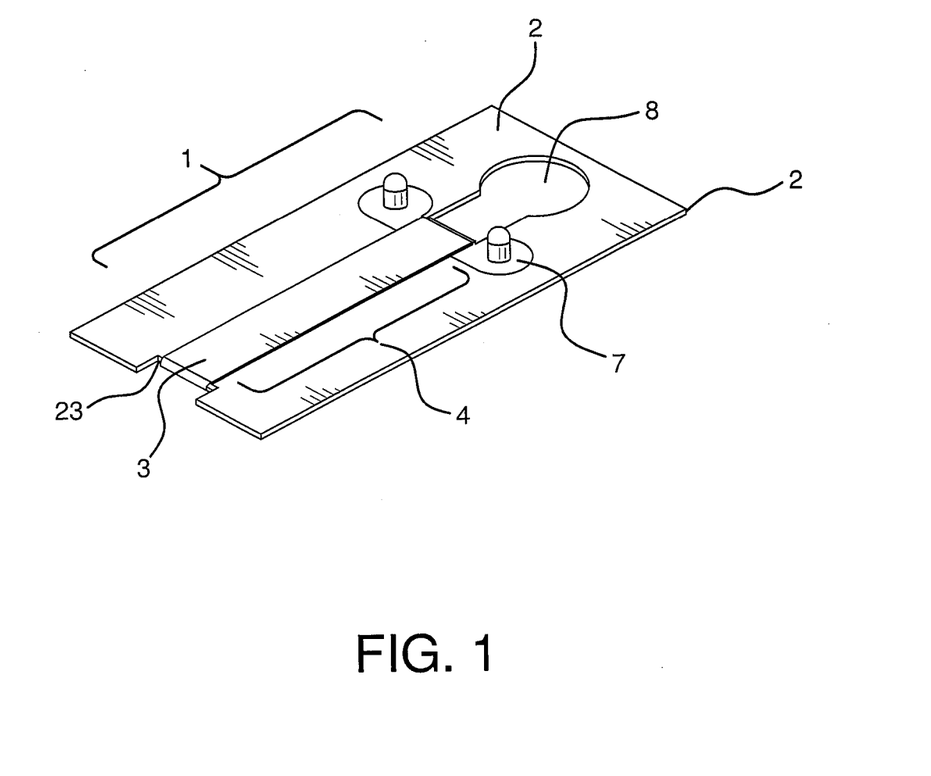
FIG. 1 is a drawing of an embodiment of an apparatus of the present invention.
Figure 2:
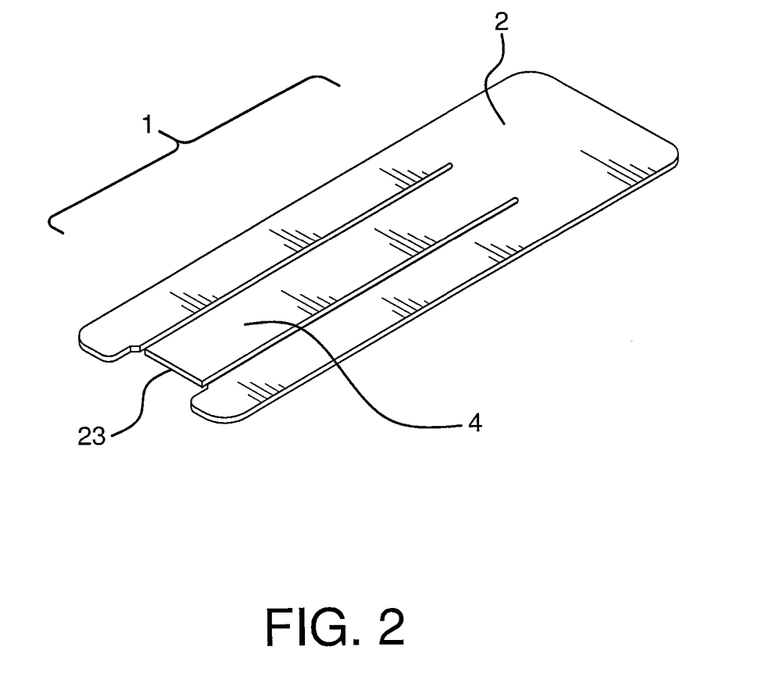
FIG. 2 is a drawing of an embodiment of an apparatus of the present invention with a hinged body.

FIG. 1 shows a schematic of the apparatus comprising a body having a first side (illustrated in this Figure as oriented on the top of the apparatus) and a second side. The body 2 of the apparatus also has a first portion and a second portion. The first portion 4 of the body is pivotable with respect to the second portion of the body. For clarity of the invention it is to be understood that the pivotable portion of the body as hereinafter described, is considered to be the first portion 4 of the body of the apparatus. A surgical reinforcement material, hereinafter referred to as "buttress material" is further disposed over an area of the first portion 4 of said body. In one embodiment the buttress material 3 is secured to the second portion of the body. The body is be sized appropriately to receive a surgical stapler in a manner that permits application of the buttress material 3 onto the jaws of the stapler.

The body has a first side 40 and a second side 50 that may be interchangeable for ease of loading a surgical stapler with buttress material. While FIG. 1 illustrates the pivotable first portion 4 of the body 2 as being located in a relative central position with respect to the remainder of the body 2, it is understood that the pivotable portion 4 may be located in other desired positions. The pivotable first portion 4 of the body functions to break the buttress material 3 at perforated areas (such as perforated tabs) so that the buttress material is easily freed from securements 7 on the apparatus. For example, the pivoting first portion bends out of the plane of the apparatus in at least one direction to separate the buttress material 3 at designated areas to prepare for application. The pivoting portion (first portion 4 of the body) of the apparatus is shown as a rectangular shaped portion, however, it is to be understood that other suitable shapes such as rods, loops, wires, rigid meshes, thin strip members, or other shapes may be desired. FIG. 1 also illustrates the body formed with an open central region 8. The open central region 8 may be incorporated into the body for ease of movement of the stapler with respect to the body.

The buttress material 3 is in contact with at least an area of the pivotable portion 4 of said body 2. Buttress material 3 suitable for use with the present invention can be fabricated from any material having acceptable biocompatibility and mechanical properties. For instance, the buttress material 3 may be formed of any suitable material and may be either synthetic or animal-derived. While synthetic materials are preferred due to, for example, their ability to be formed thinly as described herein and for other manufacturing benefits, animal-derived buttress materials may also be used. The buttress material 3 may be a single piece which is wrapped around the body of the apparatus, as shown in FIG. 1, or may be multiple pieces.

Animal-derived buttress materials (such as, for example, bovine, porcine, equine, and human products) may have difficulties associated with their placement on the working surfaces (for example the anvil and cartridge jaw surfaces) of surgical staplers. Animal-derived buttress materials cannot typically reach the consistent and thin profiles while maintaining the required strength associated with preferred synthetic buttress materials. An advantage of the present invention is that unlike traditional applications cards which do not allow successful placement of thin buttress materials, a buttress material 3 having a thickness less than 0.5 millimeters may be accurately and successfully positioned onto the working surfaces of a surgical stapler using the present apparatus.

Further, animal-derived buttress materials routinely use added steps to apply or actuate adhesives to the outer surface of their materials. For instance, some products utilize rehydration techniques, while others utilize paste-like or gel-type adhesives which need to be applied and smoothed onto the buttress material 3 prior to use. Paste-like or gel-type adhesives allow for sliding of the buttress materials on the working surfaces of a surgical stapler during loading. The present invention does not require added application or actuation steps when a ready to use adhesive such as a pressure sensitive adhesive is employed. A pressure sensitive adhesive can be ready to use by simple removal of a release liner.

An unexpected advantage of the present apparatus is that thinner buttress materials such as synthetic non-animal derived materials and other materials particularly those less than 0.5 millimeters in thickness are more readily applied to a stapler working surfaces than is possible with traditional applicator means. The buttress material 3 is able to be readily adhered or placed back to the crotch of a surgical stapler and successfully cover the staple lines with the present apparatus, because the body can be made thin enough to reach to the crotch of a stapler. This ease of placement also allows the buttress material 3 to be attached onto the working surfaces of a stapler without bunching.

Examples of suitable synthetic buttress materials include but are not limited to: bioabsorbable or biodegradable materials or webs, non-bioabsorbable materials or webs, expanded polytetrafluoroethylene ("ePTFE") such as disclosed in U.S. Pat. No. 5,810,855, synthetic materials, or other suitable buttress materials. One advantage of using synthetic buttress materials is that there is no need to rehydrate synthetic materials prior to use, and they will have a more consistent thickness. The surgical buttress material 3 may further comprise an adhesive on at least the outermost surface relative to the body of the apparatus. The adhesive may be a ready to use adhesive such as a pressure sensitive adhesive or further may be an activatable adhesive which may be moistened or otherwise activated prior to use. A release liner, such as PET release films, or other coated webs or sheets may be applied over an adhesive to protect it until it is ready for use. The release liner may be utilized to cover the buttress material 3 and pre-applied adhesive so that the liner may readily separate from the adhesive on the surgical buttress material 3, thus maintaining the integrity of the adhesive, and allowing it to be easily prepared for use. One advantage of the present apparatus is that the adhesive may be pre-applied and essentially be uniformly distributed over the buttress material. Thus, eliminating the need for any smoothing or spreading as required by unevenly distributed gel or paste-like adhesives traditionally used on buttress materials (see Example 10).

The apparatus 1 is sized to apply surgical buttress material 3 onto a surgical stapler. The apparatus may comprise the same material throughout the body or may comprise two or more different materials, such as, but not limited to plastics, metals, cardboards, foams, or any other suitable materials.

The apparatus 1 further comprises one or more securements 7 for temporarily fixing buttress material 3 to the apparatus 1. Buttress material 3 is temporarily affixed to the apparatus via this securement to allow the buttress material 3 to extend to about at least a section of the first portion 4 of the body. In one embodiment, as depicted in FIG. 1, one securement is simply an affixed tab with a perforated section formed of additional buttress material 3. The optional post is shown as additional securement means. The securements 7 are further illustrated in FIGS. 3A, 3B, and 4 as comprising a plurality of posts on each body positioned parallel to each other near the pivotable first portion 4 of the body. The posts may be designed to provide tension on the buttress material 3 so that the buttress material 3 is stretched flat, with reduced bunching or wrinkling and provide a more even contact surface to adhere onto a stapler arm. It is to be understood that the posts can be positioned non-parallel to each other in alternate embodiments. These posts are sized and positioned on the bodies to fit perforations in the surgical buttress material 3. Other forms of securement 7 include tabs with adhesive bonding, frictional interference, ultrasonic or thermal welding, mechanical attachments, or any other suitable means of securing the buttress material to the body.

Figure 3A:
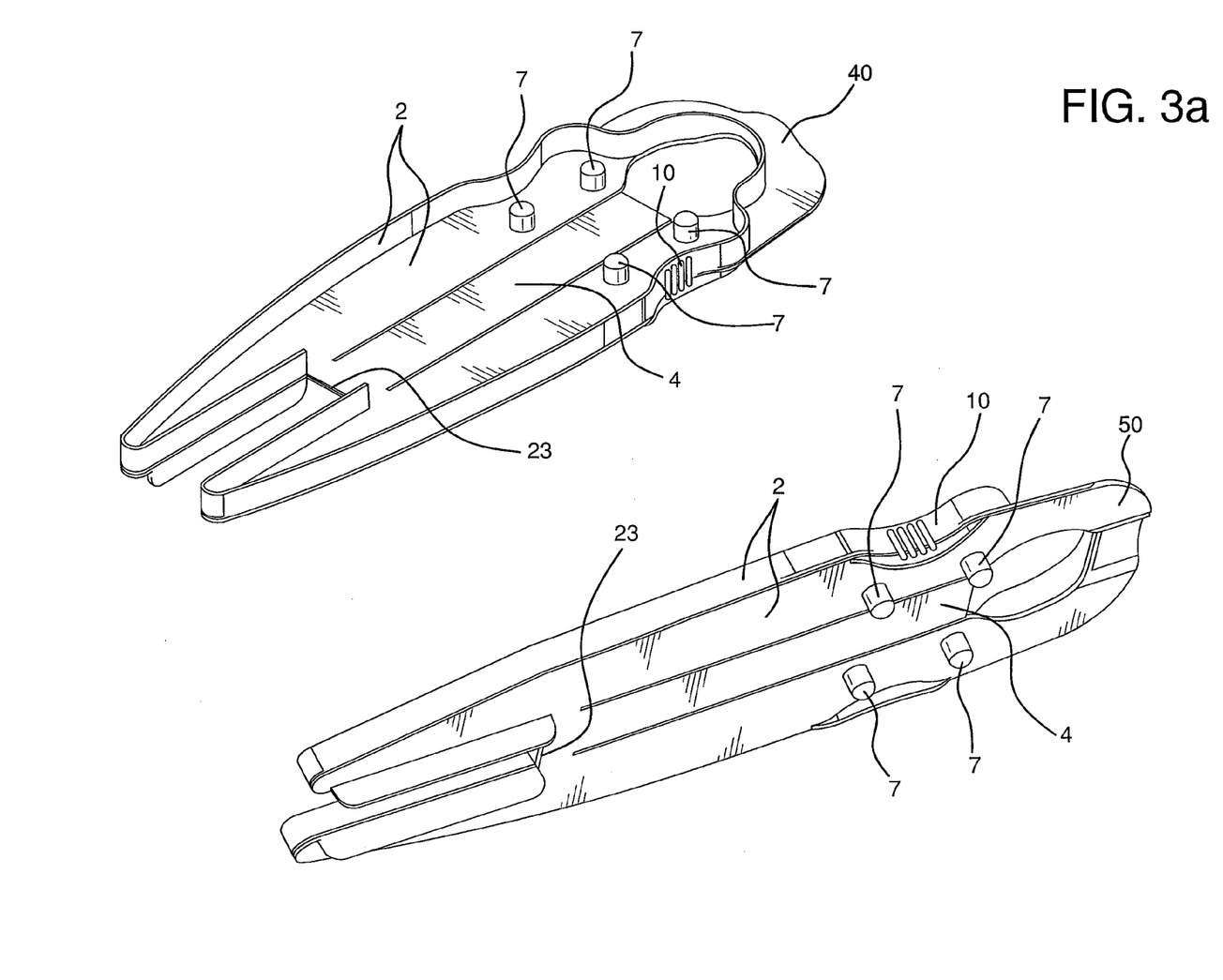
FIG. 3A is a drawing of an embodiment of a reversible apparatus of the present invention exhibiting securements in the form of posts.
Figure 3B:
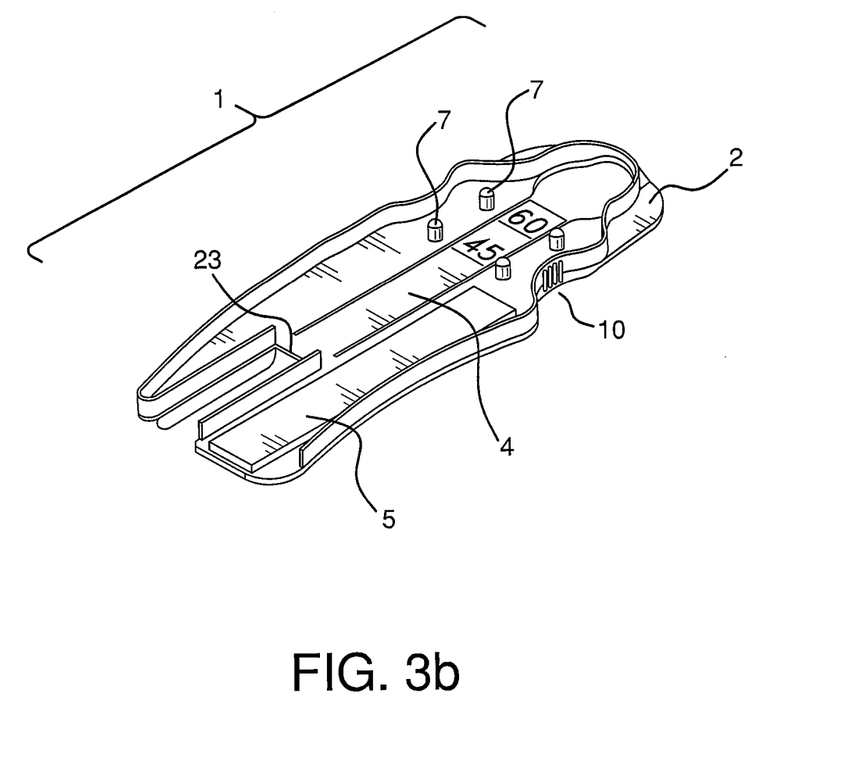
FIG. 3B is a drawing of an embodiment of an apparatus of the present invention exhibiting securements in the form of posts and an optional touch-up pad.
Figure 4:
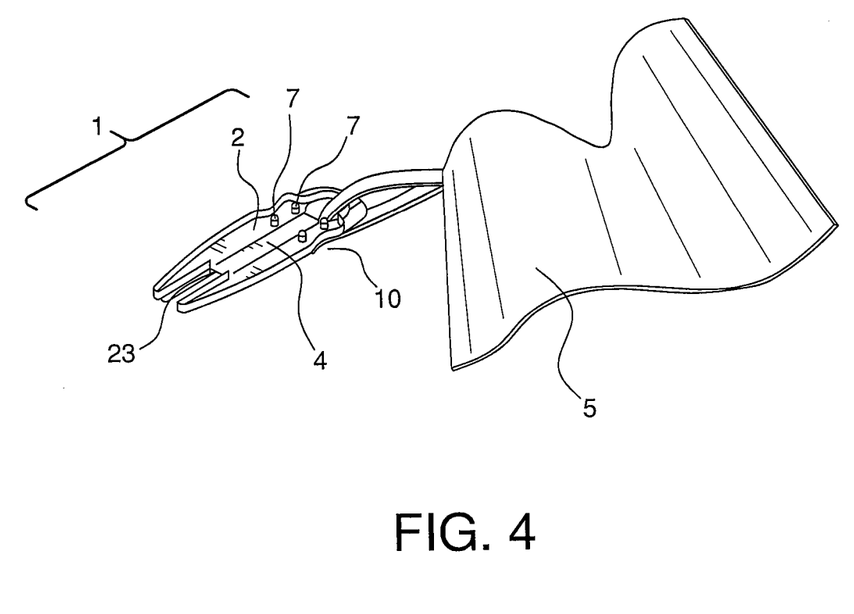
FIG. 4 is a drawing of an embodiment of an apparatus of the present invention showing an optional touch-up pad attached to the body via a connecting means.
Figure 5A:
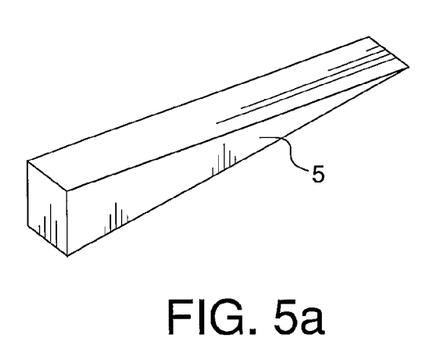
FIGS. 5A through 5D are drawings showing different embodiments of touch up pads useful in the present invention.
Figure 5B:
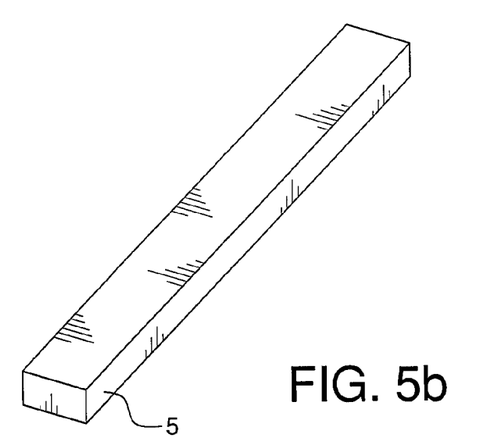
Figures 5C, 5D:
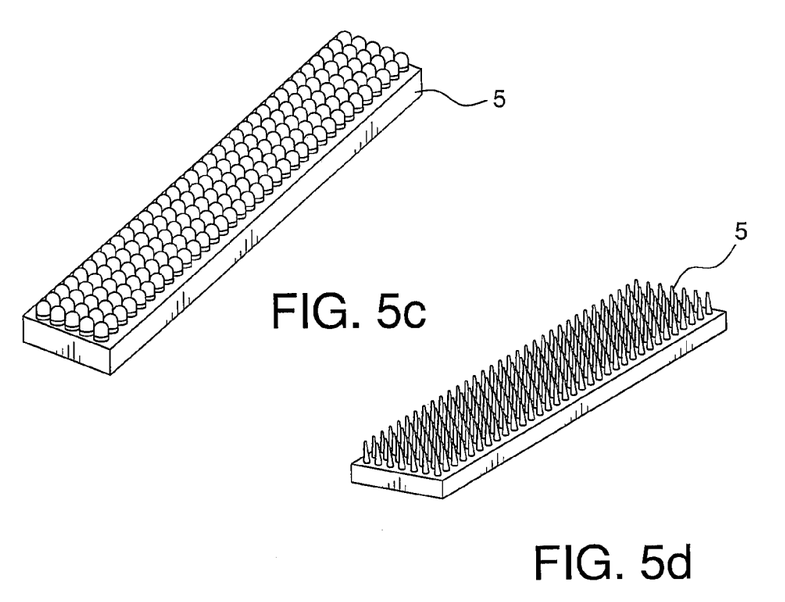

As shown in FIGS. 3A, 3B, 4, 5A-D, and 6A-6E, the apparatus of the present invention may further comprise a touch-up pad 5. FIG. 4 illustrates a touch-up pad 5 which may be permanently or removably attached to the apparatus as an interconnected element. Alternatively, as shown in FIG. 3A shows an embodiment of the present apparatus which allows the body of the apparatus to be reversibly inserted into a surgical stapler and perform in either inserted configuration. The reversible embodiment of the apparatus comprises a body having a first side 40 and a second side 50 which may be fed into a stapler irrespective of which side is in contact with the anvil and which side is in contact with the cartridge of the stapler. The reversible configuration enables a practitioner the ability to easily load the body into the stapler. Also shown in FIG. 3B and 5, an optional touch-up pad 5 may be permanently or non-permanently attached to the body of the apparatus on one or both sides. The touch-up pad is used to maximize the surface area contact between the buttress material 3 and the working surface of the stapler. For instance, adhesive 6 on the outermost facing portion of buttress material 3 adheres the buttress material 3 onto opposed working surfaces of a surgical stapler. After the buttress material is oriented onto the apparatus, it is sometimes desired that the buttress material be further pressed onto a touch pad to adhere the buttress material onto a larger surface area of the stapler. This is especially advantageous when the adhesive on the apparatus is a pressure sensitive adhesive disposed over the surgical buttress material.

As shown in FIGS. 5A through 5D, the touch-up pad 5 may be of a uniform or non-uniform topography, further the touch-up pad may comprise of one or multiple pieces, it may be designed as a wedge (for example, FIG. 5A), flat pad (for example, FIG. 5B), raised dots (for example, FIG. 5C), or the like. It is sometimes desirable that the touch-up pad have specific formations targeted to enhance the surface area around the staple line. The touch-up pad is generally a material such as, but not limited to cottons, polyesters, foams, plastics, metals, or any other suitable materials. It is an advantage to have the touch up pad located in an area apart from the buttress material 3 so that no added thickness or bulk is associated with the buttress material, or apparatus, during application of the material to the arms of the stapler.

In the embodiment shown in FIGS. 3, 4 and 6A through 6E, the body of the apparatus 1 is shaped to include a finger grip 10 to facilitate gripping of the apparatus during loading of a surgical stapler with surgical buttress material 3. The end of the apparatus proximal to the pivotable first portion 4 of the body further comprises a stapler restraining area 23. The stapler restraining area 23 defines the origin or the receiving area for the buttress material (not shown) on the pivotable portion 4 of the body. The created pivotable portion is formed via the restraining area 23 which is in contact with the crotch of a stapler which allows pivoting of the receiving area of the first portion of the body, with respect to the plane of the second portion of the body, to affix buttress material to a stapler.

Figure 6A:
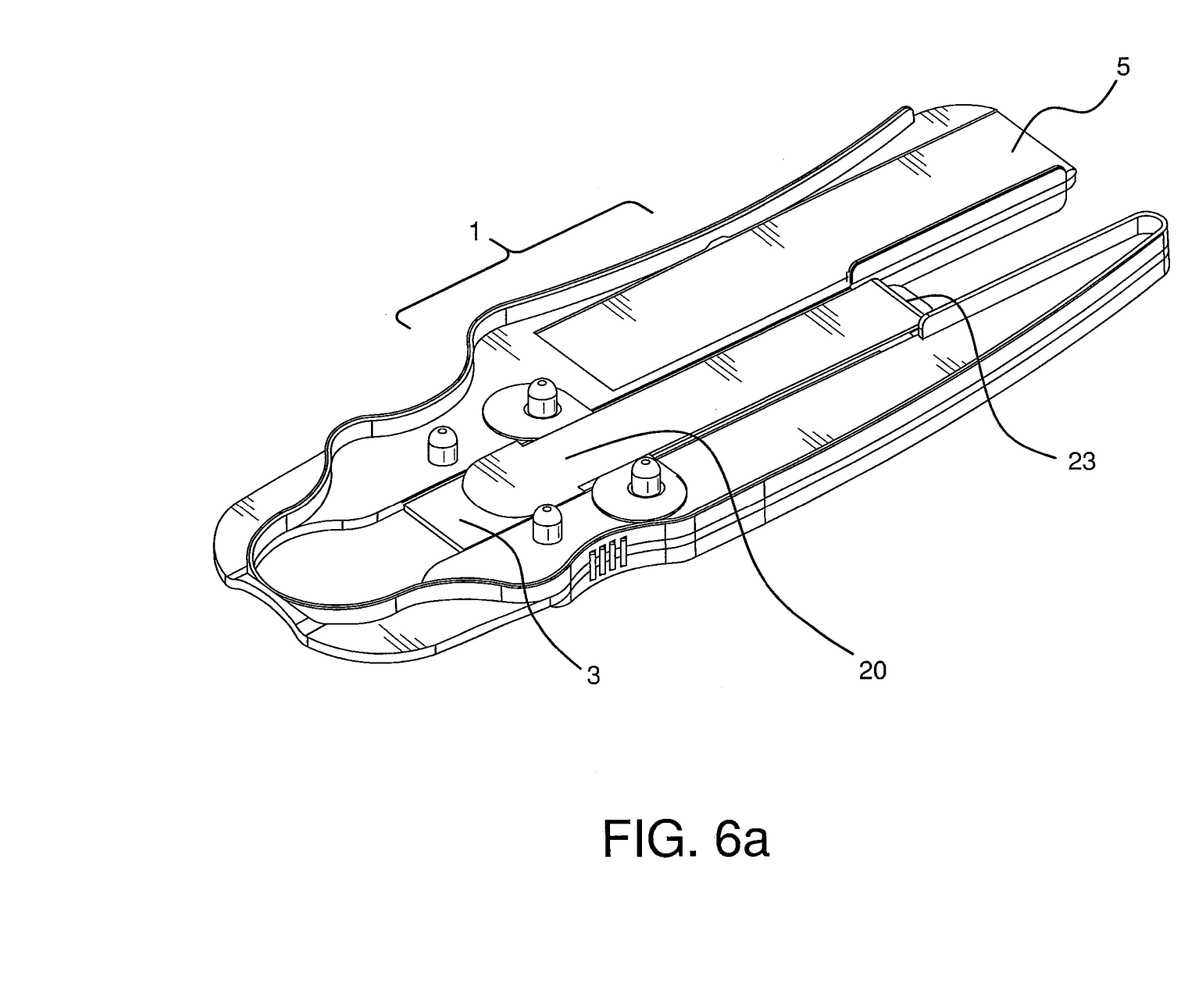
FIG. 6A through 6E are illustrations of the apparatus of the present invention with the pivoting portion of the apparatus shown bending out of the plane of the card.
Figure 6B:
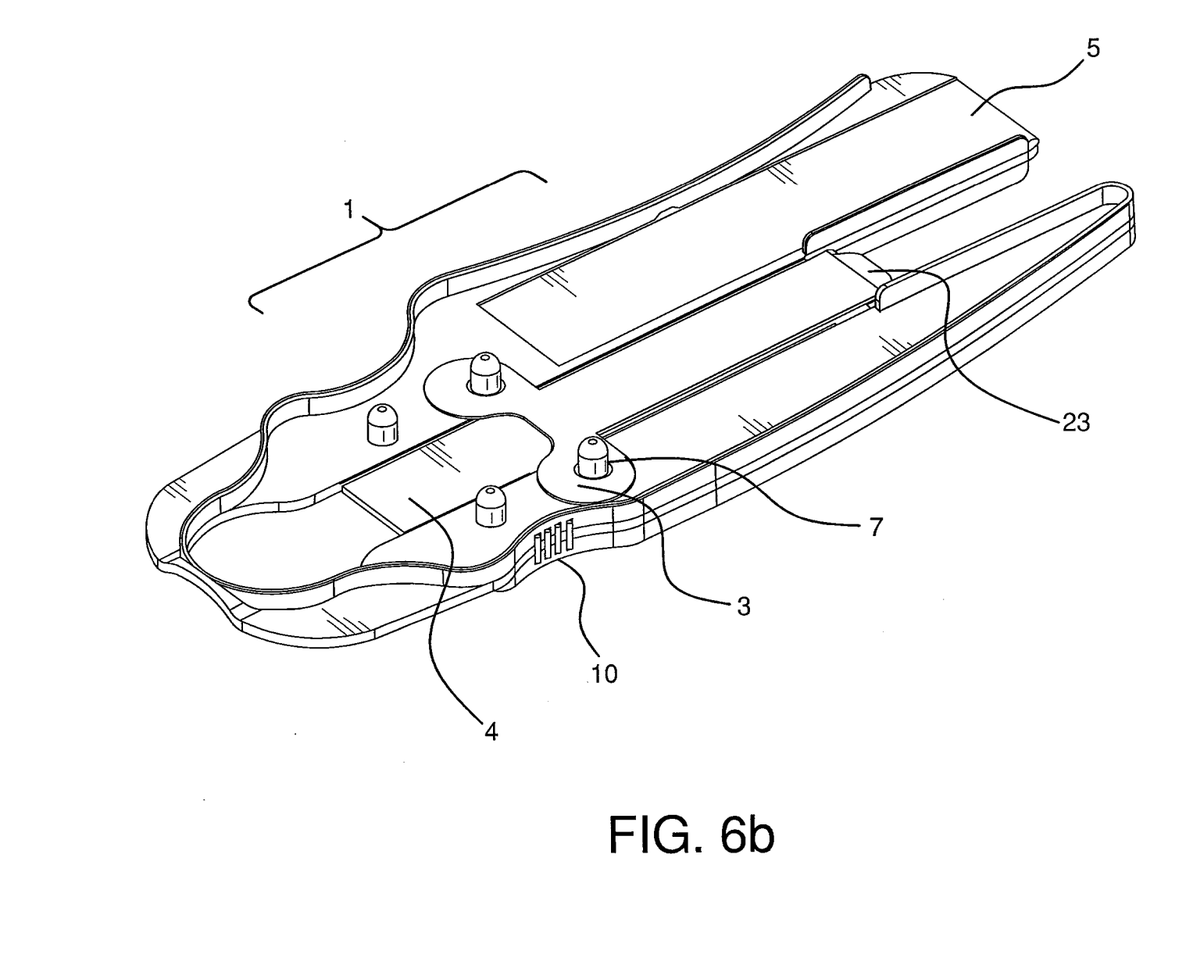
Figure 6C:
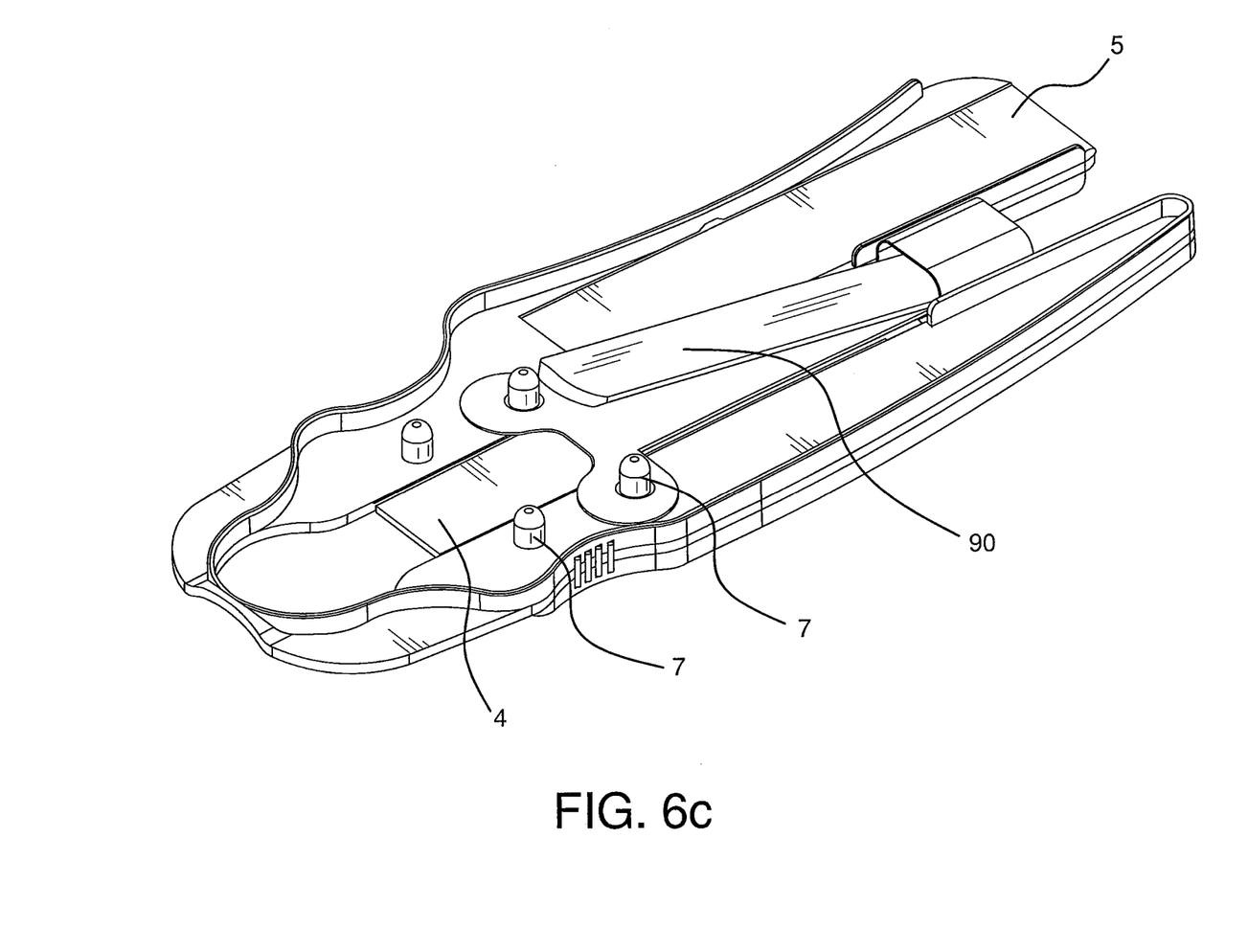
Figure 6D:
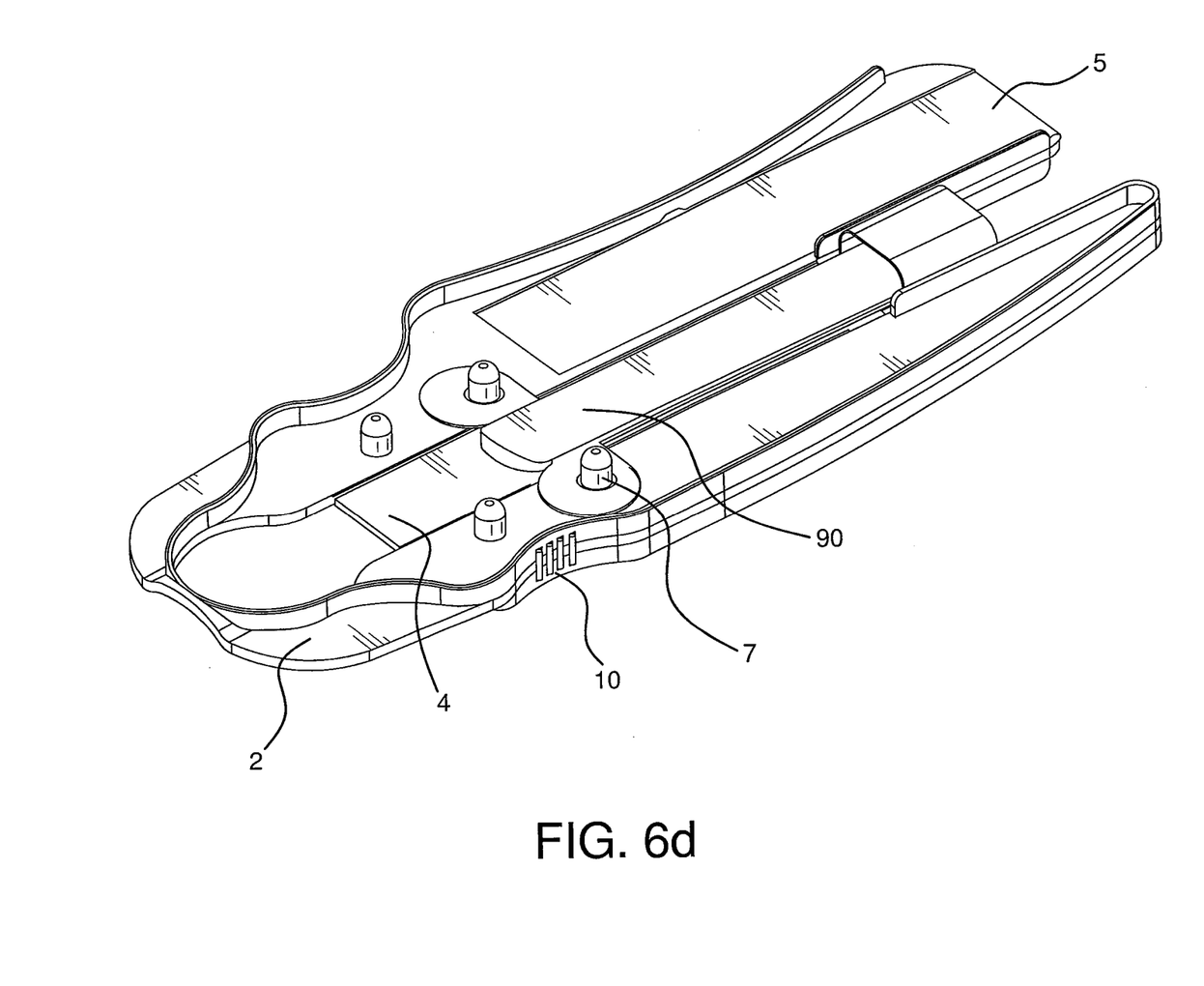
Figure 6E:
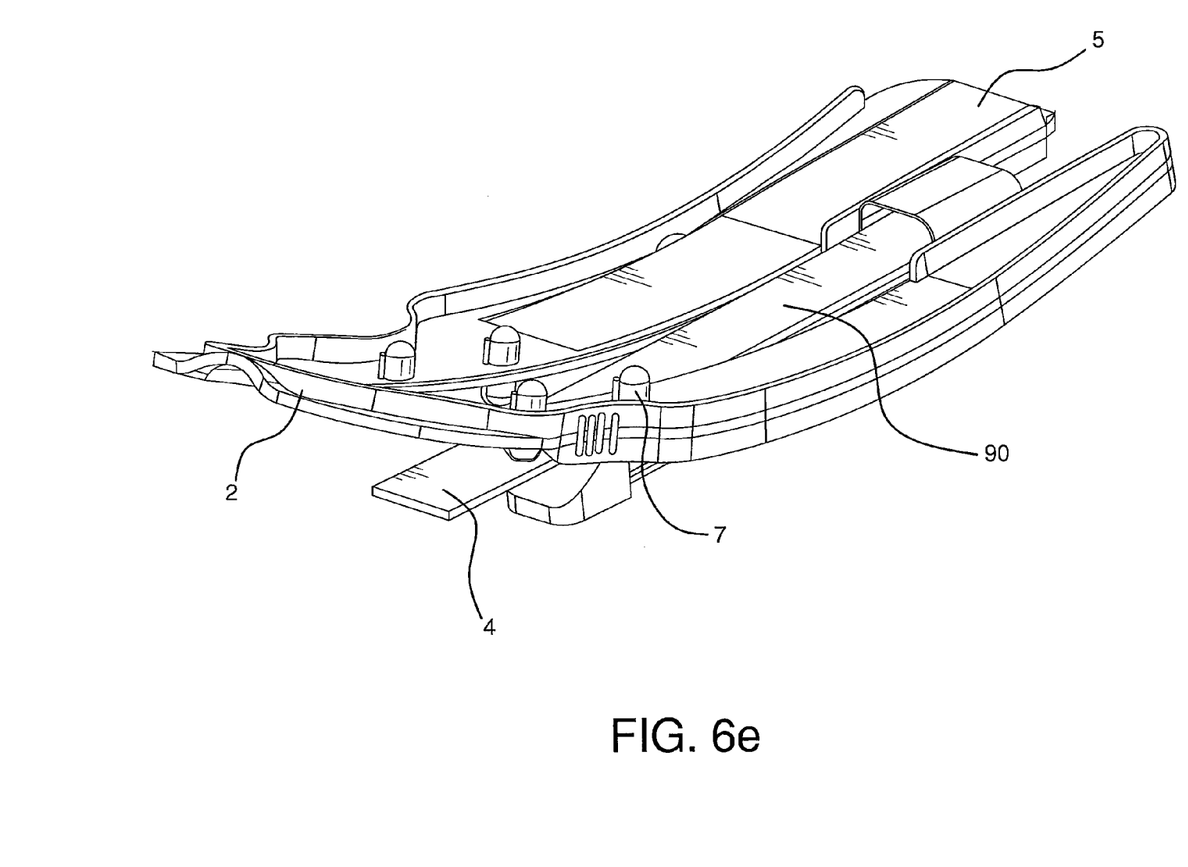

As shown in FIGS. 1 and 6A through 6E, the buttress material 3 is oriented on the body of the apparatus in order to allow a surgical stapler to clamp onto the apparatus. The adhesive 6 on the buttress material 3 adheres the buttress material 3 onto the opposed working surfaces of the surgical stapler. It is advantageous when the adhesive on the apparatus is a pressure sensitive adhesive disposed over the surgical buttress material. Prior to use, a release liner 20 may be utilized to cover the pressure sensitive adhesive and keep the adhesive in a ready to use form for application. Removal of the release liner exposes the pressure sensitive adhesive, thus enabling the practitioner to easily and quickly position the buttress material 3 onto the working surface of a surgical stapler. FIG. 6A shows a loaded apparatus 1 with a release liner 20 disposed over the buttress material 3. FIG. 6B shows a loaded apparatus 1 where the release liner is removed from the buttress material 3 exposing the adhesive on the buttress material and making it ready to engage with a stapler arm. FIG. 6C shows a stapler jaw 90 and the apparatus positioned so that the exposed adhesive on the buttress material will make contact with the working surface of the stapler jaw to adhere the buttress material onto the stapler. FIG. 6D shows a stapler jaw 90 clamped onto the apparatus 1 to allow contact between the exposed adhesive on the buttress material and the working surface of the stapler. FIG. 6E shows a the first portion 4 of the body pivoting out of the plane of the second portion of the body so that the stapler jaw 90 engaged with the first portion 4 moves to break the buttress material 3 at perforated areas and free the buttress material from securements 7 on the apparatus.

Other optional features can be added to the body including color coding of the body for ease of loading; measurement ticking, non-slip portions, or other desirable variations. Ergonomic features are also within the skill of one in the art to apply to the present apparatus such as, finger holds, curved surfaces, ribs or other raised features for additional tactile feel or grip ease especially with surgical gloves.

As described above, the apparatus of the present invention provides a simple method for applying buttress material 3 to a variety of staplers. The body of the apparatus is pre-loaded with buttress material 3 either by an artisan or as purchased in a ready to use embodiment. By "pre-loaded" it is meant that the buttress material 3 is attached to at least a portion of the body which is pivotable with respect to a second portion of said body. The release liner is removed from the buttress material, exposing the adhesive on the exposed surface of the buttress material. As shown in FIG. 6, the apparatus 1 is then inserted between open stapler arms and aligned with a stapler arm so that the buttress material 3 is in position to be applied to the arms of the stapler upon contact there between. The stapler arms are closed upon the pivotable portion of the body housing the buttress material, the pivotable region of the body is moved away from the plane of the remainder of the body so that the perforated tabs of the buttress material 3 are broken. If desired the touch-up pad may be utilized to maximize the surface area of the buttress material adhered to the stapler arms. The stapler arms are then opened to complete the transfer of the buttress material 3 to the stapler arms. The body of the apparatus is then removed from the stapler arms and discarded and the stapler is ready for use.

EXAMPLES

Example 1

A 30 mil (0.076 cm) thick card forming the body of the apparatus (dimension 10 cm L×5.7 cm W) was made by injection molding polycarbonate and configured to aid in applying surgical staple line buttress (SLR) material to the jaws of a commercially available stapler. The SLR receiving area, stapler restraining area and the pivot of the SLR card were created through a three-sided cutout (S1×S2×S3) of the polycarbonate card using a razor tool. The lengths of the longitudinal cuts (S1 & S3) on the card are about ~50% of the polycarbonate card (approximately 4.7 cm) and starting approximately 0.6 cm from one end of the card. The length of the latitudinal cut (S2) is sized to accommodate the width of the SLR and jaws of a commercially available stapler (approximately 1 cm).

The receiving area is defined by the three sides of the S1, S2 and S3 cuts. The uncut side of the receiving area defines the pivot. The end of the card closest to the pivot is the stapler restraining area. The restraining area defines the origin or the receiving area. The created pivot allows pivoting of the SLR receiving area with respect to the plane of the polycarbonate card.

Example 2

One piece of SLR material with one side having a pressure sensitive adhesive (PSA) with a release liner for covering the PSA is placed on the receiving area of the polycarbonate card prepared as in Example 1.

The SLR material is precut with connected perforated tabs that extend beyond the width of the receiving area.

The SLR material is adapted to fit onto the receiving area and can be attached to the polycarbonate card on each side with perforated tabs that extend past the width of the receiving area. The perforated tabs of the SLR are attached to the polycarbonate card using a second PSA on the opposite side of the first PSA liner.

Example 3

For a ready-to-use SLR card, the SLR is attached to the polycarbonate card prior to packaging.

Example 4

After attaching the SLR to the polycarbonate card, the release liner covering the PSA is peeled back and removed. Next, the stapler is positioned against the restraining area of the card and then clamped over the polycarbonate card receiving area on the SLR with the PSA exposed adhesive. This securely attaches the stapler to the SLR. Next the card is moved perpendicularly to the stapler jaws at the opposing end of the restraining area to break the SLR from the perforated tabs. This releases the SLR from the card and allows the SLR to transfer completely to the stapler.

Example 5

A 30 mil (0.076 cm) thick card (dimension 10.5 cm L×3 cm W) was made by injection molding polypropylene and configured to aid in applying SLR material to the jaws of a commercially available stapler. The injection molded card was designed to incorporate the SLR receiving area, stapler restraining area, and the pivot (as in example 1) in the mold design. Additionally, deformable posts were included in the design.

A receding section (dimension 2.7 cm L×1.2 cm W) is included in the design of the card such that the recession is adjacent to the restraining area on the opposite side of the receiving area. The receding section assists docking and positioning of the stapler jaws on the receiving area.

A precut SLR material (as in Example 2) with perforated tabs was adapted with holes to fit over the deformable posts. After positioning the SLR material onto the receiving area of the card, and positioning the perforated tabs over the deformable posts, the deformable posts were thermally deformed to capture the tabs and secure the SLR material to the card. Ultrasonic energy was used to thermally deform the posts.

Next the card is moved perpendicularly to the stapler jaws at the opposing end of the restraining area to break the SLR from the perforated tabs. This releases the SLR from the card and allows the SLR to transfer completely to the stapler.

Example 6

A card with similar dimensions to Example 5 was created using stereolithography apparatus (SLA). The design of this card was modified to better adapt the card to a surgical stapler by creating a receiving area that is thicker at the distal end of the card than at the proximal end of the card. Additionally the receding section of the card was modified to allow the card and precut SLR material to be positioned within the crotch of the stapler and cover all cartridge and anvil holes.

Example 7

The card per example 6 was further modified to include a touch up pad, 2.5"×0.5"×0.04" (l×w×thickness), made from the same material as the precut SLR.

The following three examples are intended to be comparative examples illustrating the advantages of the present invention against alternative devices. These examples are not necessarily embodiments of the present invention (although they may be) but serve to highlight various important aspects of the invention. For example, comparative Example 8 highlights the concept that a thin plastic application card of the present invention is preferable to a necessarily thicker application device that includes a foam receiving area. Comparative Example 9 highlights the concept that a thin synthetic buttress material fabricated with a uniform adhesive coating as in an embodiment of the present invention has desirable characteristics as compared to an application device such as that described in U.S. Pat. No. 5,752,965, which applies an adhesive gel or the like that requires a foam-type resilient equalization means to establish a uniform adhesion.

Comparative Example 8

The card per example 5 was modified by adding a 0.2" rib around the card for ergonomic ease. Addition of the rib made the card less flexible. This change also provided the card with additional stiffness to aid deployment, especially while pivoting the card.

Comparative Example 9

A card comprised of a foam receiving area (approximately 0.125" thickness) was constructed and a precut SLR material and a pressure sensitive adhesive was attached to the foam via clips. The SLR was then positioned onto a surgical stapler in the same manner as in Example 4. Upon positioning the SLR into the stapler, the thickness of the foam card caused the SLR material to prematurely touch the stapler causing the SLR material to bunch and not cover the entire staple line.

Comparative Example 10

A Peri-Strips Dry dispenser (Synovis, Part #73133-07588, St. Paul Minn.) was modified by replacing the foam pad with a 0.035" thick polypropylene card. The supplied adhesive (Synovis, Part #7300-101023, St. Paul Minn.) was then added in a continuous bead to the SLR material, per instructions for use, and the assembly was positioned within the working surface of the stapler jaws. The supplied adhesive was gel-like in nature, and required pressure to evenly distribute the adhesive onto the material. The stapler (Ethicon, Proximate 75, Cincinnati Ohio) was then closed and then re-opened to examine the deployment of the SLR onto the stapler jaws. The SLR material did adhere to the working surface of the stapler at the center of the buttress material where the bead was applied, but the adhesive was not evenly distributed across the entire width of the SLR to adhere the edges of the SLR to the stapler.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An apparatus for supplying surgical reinforcement material to a surgical stapler, said apparatus comprising:
    a card having a first portion, a second portion and a pivot; said first portion being pivotable with respect to said second portion about said pivot; and
    a surgical buttress material disposed over said first portion and secured to said second portion,
    wherein the buttress material is adapted to release from said second portion, upon pivoting of said first portion relative to said second portion.

2. The apparatus of claim 1 further comprising a touch-up pad attached to said second portion of said card.

3. The apparatus of claim 1 further comprising a securement for temporarily fixing a surgical buttress material to said second portion of said card.

4. The apparatus as set forth in claim 1 further comprising an adhesive disposed over said surgical buttress material.

5. The apparatus as set forth in claim 4 wherein the adhesive is a pressure sensitive adhesive.

6. The apparatus as set forth in claim 4 further comprising a release liner disposed over said adhesive.

7. The apparatus as set forth in claim 4 wherein the adhesive is preapplied in an essentially uniform layer over the surgical buttress material.

8. The apparatus of claim 1 wherein the buttress material is a synthetic buttress material.

9. The apparatus of claim 8 wherein the synthetic buttress material is bioabsorbable.

10. The apparatus of claim 1 wherein the buttress material is less than 0.5 millimeter thick.

11. An apparatus for supplying surgical reinforcement material to a surgical stapler, said apparatus comprising:
    a card having a first portion, a second portion and a pivot; said first portion being pivotable with respect to said second portion about said pivot; and
    a surgical buttress material disposed over said first portion and secured to said second portion;
    wherein said card has a first side and a second side that are reversible such that said apparatus may be fed to a stapler irrespective of which side is in contact with a stapler anvil and which side is in contact with a stapler cartridge, and
    wherein the buttress material is adapted to release from said second portion upon pivoting of said first portion relative to said second portion.

12. An apparatus for supplying surgical reinforcement material to a surgical stapler, said apparatus comprising a card having a synthetic buttress material attached to a portion of said card, a pressure sensitive adhesive uniformly distributed over the surgical buttress material with respect to said card, a release liner disposed over said pressure sensitive adhesive, the portion of said card having the buttress material thereon being pivotable with respect to the remainder of said card about a pivot, wherein the pressure sensitive adhesive is of a form suitable for use upon removal of said release liner and wherein the buttress material is adapted to be released from the portion of said card upon pivoting the portion of said card relative to the remainder of said card about said pivot.

13. A kit comprising:
    a) an apparatus for supplying surgical reinforcement material to a surgical stapler; said apparatus comprising a card having a first portion, a second portion and a pivot; said first portion being pivotable with respect to said second portion about said pivot;
    b) a surgical buttress material disposed over said first portion and secured to said second portion of said apparatus wherein the buttress material is adapted to be released from said first portion upon pivoting said first portion relative to said second portion:
    c) a surgical stapler; and
    d) instructions for releasably affixing said buttress material on said surgical stapler.

14. The kit of claim 13 further comprising a touch-up pad.

15. A method for releasably affixing surgical buttress material to a surgical stapler comprising the steps of:
    a) obtaining an apparatus for supplying surgical reinforcement material to a surgical stapler; said apparatus comprising a card having a first portion, a second portion and a pivot; said first portion being pivotable with respect to said second portion about said pivot; and wherein said first portion has a buttress material that is adapted to be released from said first portion upon pivoting said first portion relative to said second portion about said pivot;
    b) inserting the apparatus between open stapler arms;
    c) orienting the stapler arms so that the buttress material is in position to be applied to the arms of the stapler upon contact there between;
    d) closing stapler arms upon the buttress material;
    e) moving the pivotable region of the card away from the plane of the remainder of the card;
    f) opening the stapler arms; and
    g) removing the card from contact with the stapler arms.

16. A method for releasably affixing surgical buttress material to a surgical stapler comprising the steps of:
    a) obtaining an apparatus for supplying surgical reinforcement material to a surgical stapler, said apparatus comprising a card having a first portion, a second portion and a pivot; said first portion being pivotable with respect to said second portion about said pivot; and wherein said first portion has a buttress material thereon that is adapted to be released from said first portion upon pivoting said first portion relative to said second portion;
    b) inserting the apparatus between open stapler arms;
    c) orienting the stapler arms so that the buttress material is in position to be applied to the arms of the stapler upon contact there between;
    d) removing a release liner from the apparatus to expose a ready to use pressure sensitive adhesive on the outermost surface of the buttress material;
    e) closing the stapler arms upon the buttress material;
    f) moving the pivotable region of the body away from the plane of the remainder of the card;
    g) opening the stapler arms; and
    h) removing the card from contact with the stapler arms so that the buttress material is adhered onto the stapler arms.

17. An apparatus for supplying surgical reinforcement material to a surgical stapler, said apparatus comprising:
    a card having a first portion, a second portion and a pivot; said first portion being pivotable with respect to said second portion about said pivot;

a touch up pad; and
a surgical buttress material disposed over said first portion and secured to said second portion,
wherein the buttress material is adapted to be released from said first portion upon pivoting said first portion relative to said second portion.

* * * * *